(12) United States Patent
Lancelot

(10) Patent No.: US 11,232,855 B2
(45) Date of Patent: Jan. 25, 2022

(54) NEAR-REAL-TIME TRANSMISSION OF SERIAL PATIENT DATA TO THIRD-PARTY SYSTEMS

(71) Applicant: AirStrip IP Holdings, LLC, San Antonio, TX (US)

(72) Inventor: Jean-Francois Lancelot, San Diego, CA (US)

(73) Assignee: AirStrip IP Holdings, LLC, San Antonio, TX (US)

( * ) Notice: Subject to any disclaimer, the term of this patent is extended or adjusted under 35 U.S.C. 154(b) by 269 days.

(21) Appl. No.: 15/513,963

(22) PCT Filed: Sep. 3, 2015

(86) PCT No.: PCT/US2015/048333
§ 371 (c)(1),
(2) Date: Mar. 23, 2017

(87) PCT Pub. No.: WO2016/048619
PCT Pub. Date: Mar. 31, 2016

(65) Prior Publication Data
US 2017/0249435 A1 Aug. 31, 2017

Related U.S. Application Data

(60) Provisional application No. 62/053,948, filed on Sep. 23, 2014.

(51) Int. Cl.
*G16H 10/60* (2018.01)
*G16H 20/10* (2018.01)
(Continued)

(52) U.S. Cl.
CPC ......... *G16H 10/60* (2018.01); *G06F 21/6245* (2013.01); *G16H 20/10* (2018.01); *G16H 40/67* (2018.01)

(58) Field of Classification Search
CPC ............ G06F 19/3418; G06F 19/3456; G06F 21/6245; G16H 10/60; G06Q 50/24
(Continued)

(56) References Cited

U.S. PATENT DOCUMENTS 7,433,827 B2* 10/2008 Rosenfeld ............... G16H 50/20
705/2
7,490,048 B2* 2/2009 Joao ....................... G06F 19/328
705/3
(Continued)

OTHER PUBLICATIONS

Search Report and Written Opinion for International Application No. PCT/US2015/048333, dated Dec. 4, 2015, 13 pages.
(Continued)

*Primary Examiner* — Rachel L. Porter
*Assistant Examiner* — Steven G Sanghera
(74) *Attorney, Agent, or Firm* — Fish & Richardson P.C.

(57) ABSTRACT

Implementations for providing patient physiological data to a third-party system in near-real-time include determining that a value of a data element within a data source has changed, and determining that the data element is included in a watchlist, the watchlist including one or more topics, each topic being associated with at least one data element, and in response: providing a data element tuple associated with the data element, and transmitting the data element tuple to the third-party system over a network. Other implementations of this aspect include corresponding systems, apparatus, and computer programs, configured to perform the actions of the methods, encoded on computer storage devices.

11 Claims, 8 Drawing Sheets

(51) Int. Cl.
*G16H 40/67* (2018.01)
*G06F 21/62* (2013.01)

(58) Field of Classification Search
USPC .......................................................... 705/3
See application file for complete search history.

(56) References Cited

U.S. PATENT DOCUMENTS

| | | | |
|---|---|---|---|
| 8,626,533 B2 | 1/2014 | Rao et al. | |
| 8,775,202 B2* | 7/2014 | Hanf | G06Q 10/10 |
| | | | 705/2 |
| 9,317,429 B2* | 4/2016 | Ramanujan | G06F 12/0238 |
| 9,542,647 B1* | 1/2017 | Mirhaji | G06F 17/274 |
| 2002/0077849 A1* | 6/2002 | Baruch | G16H 70/60 |
| | | | 705/2 |
| 2002/0198739 A1* | 12/2002 | Lau | G06F 16/288 |
| | | | 705/3 |
| 2007/0150311 A1* | 6/2007 | Lazerus | G16H 80/00 |
| | | | 705/2 |
| 2007/0156966 A1* | 7/2007 | Sundarrajan | G06F 12/0813 |
| | | | 711/133 |
| 2007/0220086 A1* | 9/2007 | Goldberg | G06Q 10/10 |
| | | | 709/203 |
| 2010/0250236 A1* | 9/2010 | Jagannathan | G10L 15/1822 |
| | | | 704/9 |
| 2011/0202556 A1* | 8/2011 | Fernandez | G06F 19/328 |
| | | | 707/769 |
| 2012/0110016 A1* | 5/2012 | Phillips | G06Q 10/06 |
| | | | 707/780 |
| 2013/0197938 A1* | 8/2013 | Bayouk | G16H 10/60 |
| | | | 705/3 |
| 2014/0014720 A1* | 1/2014 | Sarkis, Jr. | G06Q 50/22 |
| | | | 235/382 |
| 2014/0249854 A1* | 9/2014 | Moore | G16H 10/60 |
| | | | 705/3 |
| 2016/0048700 A1* | 2/2016 | Stransky-Heilkron | G06F 21/34 |
| | | | 707/785 |

OTHER PUBLICATIONS

International Preliminary Report on Patentability for International Application No. PCT/US2015/048333, dated Apr. 6, 2017, 7 pages.

* cited by examiner

NEAR-REAL-TIME TRANSMISSION OF SERIAL PATIENT DATA TO THIRD-PARTY SYSTEMS

CROSS-REFERENCE TO RELATED APPLICATIONS

This application is a U.S. National Stage Application under 35 USC § 371 and claims the benefit of International Patent Application No. PCT/US2015/048333, filed on Sep. 3, 2015, which claims priority to U.S. Provisional Application No. 62/053,948, filed on Sep. 23, 2014. The entire contents of the foregoing applications are incorporated herein by reference.

BACKGROUND

Patient information can be stored across multiple facilities associated with respective health care providers. For example, healthcare continua can include hospitals, clinics, laboratories, and/or other healthcare facilities. In some instances, each healthcare facility had its own data source for storing patient information and data associated with services provided at the respective facility. For example, multiple, different electronic medical records (EMRs) can be provided for a particular patient across a healthcare continuum. In some examples, such EMRs are vendor-specific, storing data and information is disparate formats.

Physicians and other healthcare providers may be required to access patient data and information from across a healthcare continuum. The disparate nature, in which data and information may be stored, can complicate retrieval and display of relevant patient information to healthcare providers.

SUMMARY

Implementations of the present disclosure provide methods for providing patient physiological data to a third-party system in near-real-time. In some examples, methods include actions of determining that a value of a data element within a data source has changed, and determining that the data element is included in a watchlist, the watchlist including one or more topics, each topic being associated with at least one data element, and in response: providing a data element tuple associated with the data element, and transmitting the data element tuple to the third-party system over a network. Other implementations of this aspect include corresponding systems, apparatus, and computer programs, configured to perform the actions of the methods, encoded on computer storage devices.

These and other implementations can each optionally include one or more of the following features: the data element tuple includes one or more of the value, a time, a name, a data source name, a source identifier, and a standard identifier; the name is provided as a human-readable name for the data element, the data source name indicates the data source and/or a type of the data source, the source identifier indicates an identifier assigned to the data source, and the standard identifier comprises an identifier for the data element using an applicable healthcare standard vocabulary; the watchlist is provided as a computer-readable file; determining that the data element is included in a watchlist includes: comparing information provided from the data source to information provided in the watchlist, and determining that the information provided from the data source matches the information provided in the watchlist; the watchlist is specific to the third-party system and includes connection data for the third-party system; the connection data includes an Internet Protocol (IP) address and a transmission control protocol (TCP) port number assigned to the third-party system; the watchlist is one of a plurality of watchlists, each watchlist corresponding to a respective third-party system; and a topic includes one of a clinical score, a measure and a condition, each of which is determined based on at least one value of at least one data element.

Other aspects of the present disclosure provide systems including one or more processors, and a computer-readable medium coupled to the one or more processors having instructions stored thereon which, when executed by the one or more processors, cause the one or more processors to perform one or more of the methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Implementations of the present disclosure are generally directed to a platform and service that enables pre-identified data to flow serially out of the platform in near-real-time, as new data or changes to existing data occur on a source system, a monitor, a sensor, and/or any other appropriate source of data that communicates with the platform. In some implementations, the platform is provided as an enterprise scalable, data- and vendor-agnostic mobility architecture for processing and securely delivering patient data and information from medical devices, electronic medical records (EMRs) and patient monitors to a third-parties. An example third-party can include a third-party data analysis system that can process received data to perform one or more analytic determinations. In some examples, implementations of the present disclosure provide integration, filtering and unification of structured patient data and patient information from a plurality of data sources across a healthcare continuum. As discussed in further detail herein, implementations of the present disclosure enable timely and collaborative clinical decision-making, and enable healthcare systems to better store patient data, track quality metrics, empower a mobile workforce, expand networks, and achieve clinical transformation.

As described herein, implementations of the present disclosure enable, among others: third-party replication, in which the platform transmits data to a third-party database that replicates data from one or more connected data sources; near-real-time triggers for rule-based systems, in which the platform triggers rules based on changes in the connected data sources; a single, serialized source of clinical events for all source systems across the healthcare continuum, in which changes from connected data sources are multiplexed into single time-sequenced stream of information; a simple, universal, modern interface with standard identifiers (e.g., use of a single underlying domain model, JSON contracts, TCP/IP sockets, and standard clinical terminologies) to streamline data ingestion; and filtering.

Figure 1:
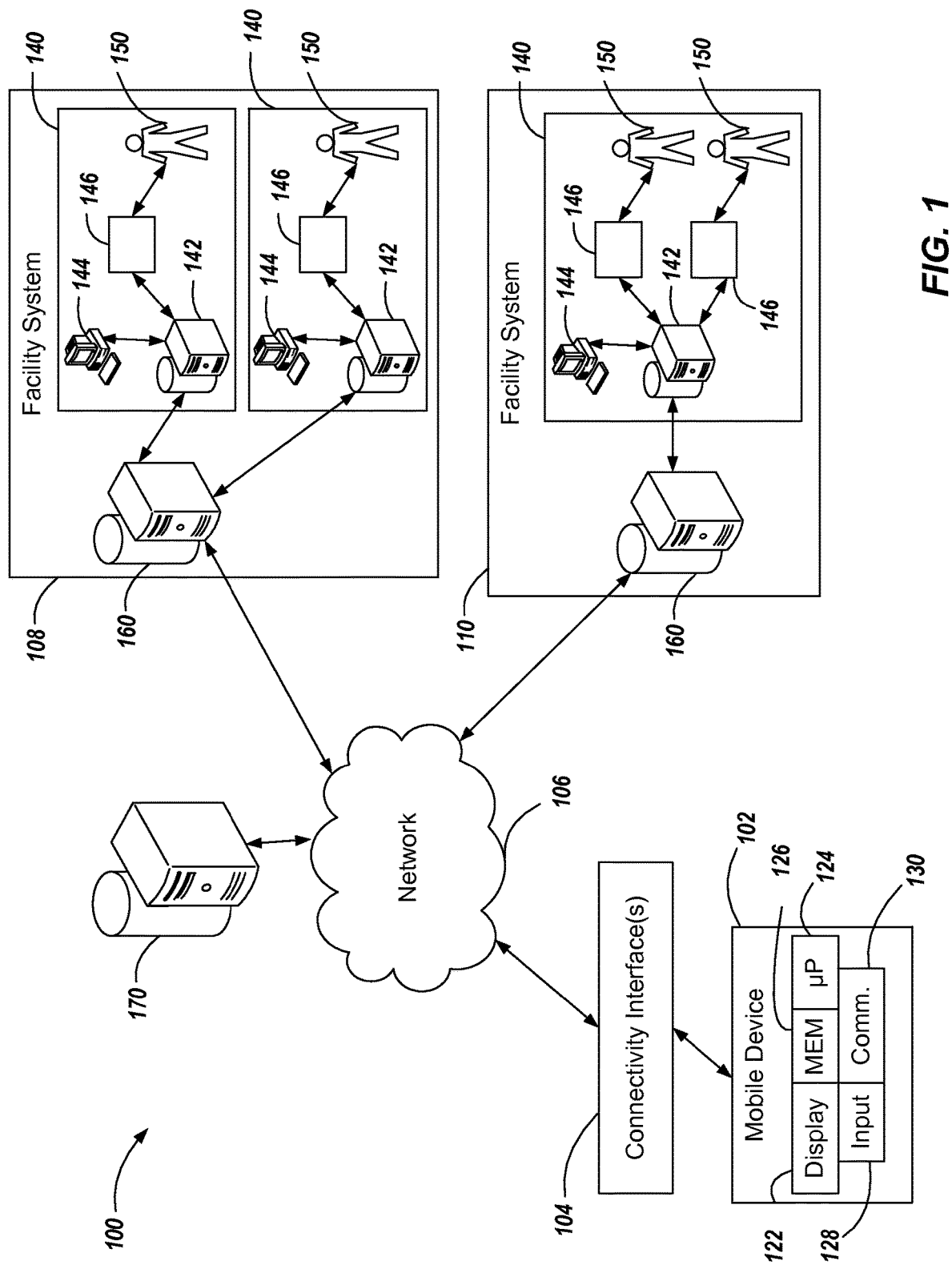
FIG. 1 is a schematic illustration of an example system architecture in accordance with implementations of the present disclosure.

Referring now to FIG. 1, an example system architecture 100 is illustrated, and includes a mobile device 102, connectivity interface(s) 104, a network 106, a first facility system 108, and a second facility system 110. As discussed in further detail herein, data is transferred from each of the first and second facility systems 108, 110 through the network 106 to a third-party analysis system 170 and through connectivity interface(s) 104 for presentation, or display on the mobile device 102. Further, data can be stored at the third-party analysis system 170. In some implementations, the data can be transferred from the mobile device 102 through the connectivity interface(s) 104 and the network 106 to each of the first and second facility systems 108, 110. Although a single mobile device 102 is illustrated, it is contemplated that one or more mobile devices 102 can communicate with each of the first and second facility systems 108, 110 through the network 106 and the connectivity interface(s) 104. Similarly, although two facility systems are illustrated, implementations of the present disclosure can include one or more facility systems.

The mobile device 102 can include any number of example devices. Such example devices include, but are not limited to, a mobile phone, a smartphone, a tablet computing device, a personal digital assistant (PDA), a laptop personal computer (PC), a desktop PC, and/or appropriate combinations thereof. In the depicted example, the mobile device 102 includes a display 122, a processor 124, memory 126, an input interface 128, and a communication interface 130. The processor 124 can process instructions for execution of implementations of the present disclosure. The instructions can include, but are not limited to, instructions stored in the memory 126 to display graphical information on the display 122. Example displays include, but are not limited to, a thin-film-transistor (TFT) liquid crystal display (LCD), or an organic light emitting diode (OLED) display. The memory 126 stores information within the mobile device 102. In some implementations, the memory 126 can include a volatile memory unit or units, and/or a non-volatile memory unit or units. In other implementations, removable memory can be provided, and can include, but is not limited to, a memory card. Example memory cards can include, but are not limited to, a secure digital (SD) memory card, a mini-SD memory card, a USB stick, and the like.

In some examples, the input interface 128 can include a keyboard, a touchscreen, a mouse, a trackball, a microphone, a touchpad, and/or appropriate combinations thereof. In some implementations, an audio codec (not shown) can be provided, which receives audible input from a user or other source through a microphone, and converts the audible input to usable digital information. The audio codec can generate audible sound, such as through a speaker that is provided with the mobile device 102. Example sounds can include sound from voice telephone calls, recorded sound (e.g., voice messages, music files, etc.), and/or sound generated by applications operating on the mobile device 102.

The mobile device 102 may communicate wirelessly through the communication interface(s) 104, which can include digital signal processing circuitry. The communication interface(s) 104 may provide communications under various modes or protocols including, but not limited to, GSM voice calls, SMS, EMS or MMS messaging, CDMA, TDMA, PDC, WCDMA, CDMA2000, and/or GPRS. Such communication may occur, for example, through a radio-frequency transceiver (not shown). Further, the mobile device can be capable of short-range communication using features including, but not limited to, Bluetooth and/or WiFi transceivers (not shown).

The mobile device 102 communicates with the network 106 through the connectivity interface(s) 104. In some examples, the connectivity interface(s) 104 can include a satellite receiver, cellular network, a Bluetooth system, a Wi-Fi system (e.g., 802.x), a cable modem, a DSL/dial-up interface, a private branch exchange (PBX) system, and/or appropriate combinations thereof. Each of these connectivity interfaces 104 enables data to be transmitted to/from the network 106. In some examples, the network 106 can be provided as a local area network (LAN), a wide area network (WAN), a wireless LAN (WLAN), a metropolitan area network (MAN), a personal area network (PAN), the Internet, and/or combinations thereof.

Figure 2:
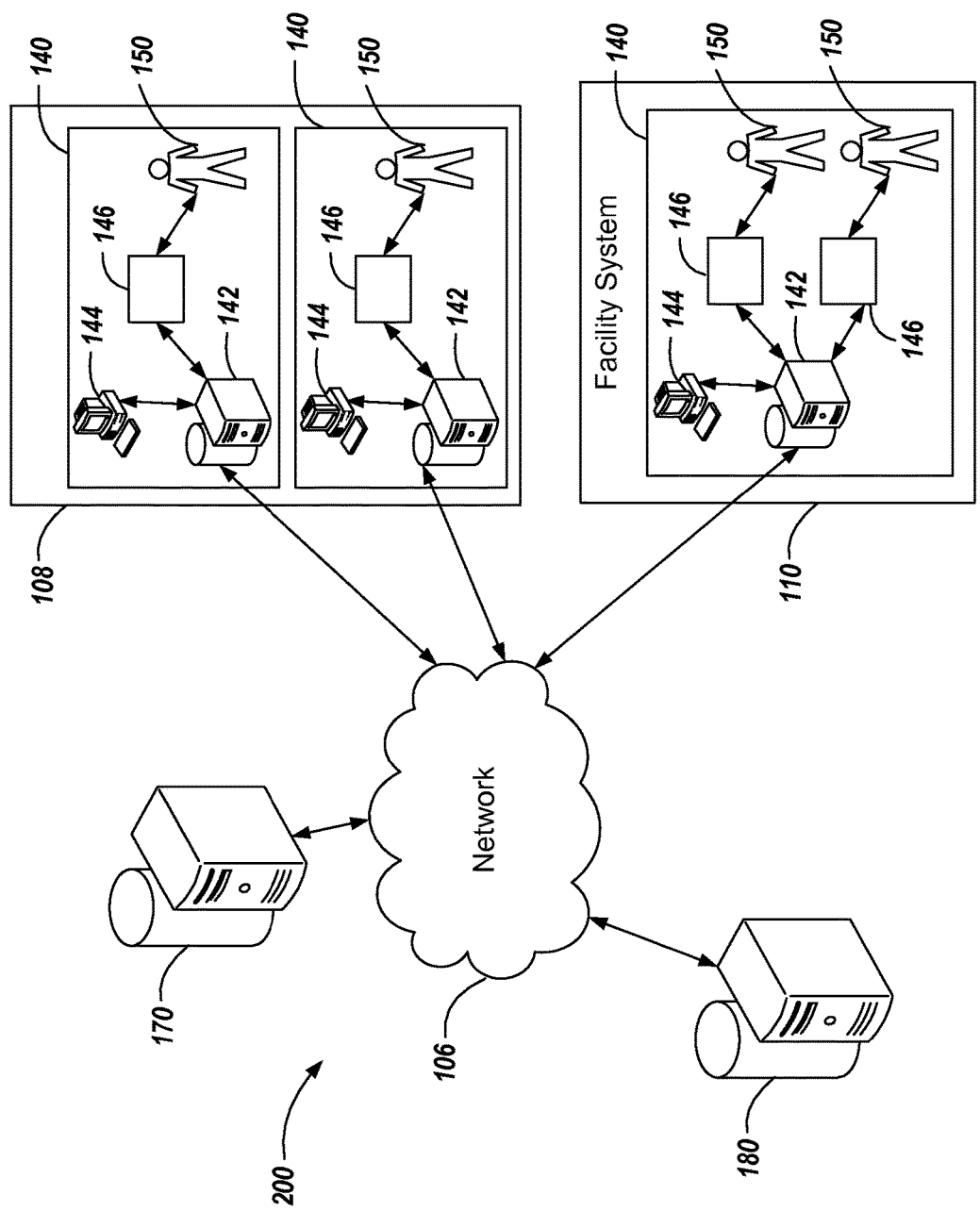
FIG. 2 is a schematic illustration of another example system architecture in accordance with implementations of the present disclosure.

In the example systems of FIGS. 1 and 2, the first facility system 108 includes a plurality of facilities 140, and the second facility system 110 includes a facility 140. It is contemplated that each facility system 108, 110 can include one or more facilities, and is not limited to the example arrangement described herein. In the case of multiple facilities, the facilities can be remotely located from one another, and/or can be located at a common location, or site (e.g., separate departments in a common (the same) building). Each facility system 108, 110 can be provided as a medical care system, for example, which medical care system can include one or more hospitals, hospital systems, clinics, physician offices, and the like.

In some examples, each facility 140 includes an associated information system 142, computer interface(s) 144, and patient monitoring device(s) 146. Example information systems can include, but are not limited to, a clinical information system (CIS), an EMR system, an electronic health record (EHR) system, and/or a hospital information system (HIS). Each information system 142 can be provided as a server, and supports the acquisition, storage, modification, and distribution of clinical information, such as patient data, throughout the facility 140 and/or facility system 108, 110. In some examples, each information system 142 can communicate with one or more ancillary information systems (not shown) that can include, but are not limited to, a pharmacy management system, a laboratory management system, and/or a radiology management system. Although the example system architecture 100 includes an information system 142 located at each facility 140, it is contemplated that the facilities 140 can communicate with a common information system 142 that is remotely located from either facility 140, or that is located at one of the facilities 140 within the facility system 108, 110.

In some examples, the computer interface 144 can communicate with the information system 142 to enable access to information that is stored within, and managed by the information system 142. In some examples, the computer interface 144 can include a personal computer (PC) (e.g., desktop, laptop, or tablet). Although a single computer interface 144 is illustrated in the example architectures described herein, it is contemplated that one or more computer interfaces 144 can communicate with the information system 142. Communication between each computer interface 144 and the information system 142 can be achieved via a direct connection, or remotely through a network (not shown) that can include, but is not limited to, a LAN, a WAN, a WLAN, and/or the Internet.

In some examples, each patient monitoring device 146 monitors physiological characteristics of a particular patient 150, and generates data signals based thereon. As discussed in further detail herein, implementations of the present disclosure provide patient monitoring devices that include a computing device, such as a tablet computing device. The data signals are communicated to the information system 142, which collects patient data based thereon, and stores the data to a patient record that is associated with the particular patient. An example patient record can include an electronic medical record (EMR). Although a single patient monitoring device 146 is illustrated per each patient 150, it is contemplated that multiple patient monitoring devices 146 can monitor a particular patient 150. The patient monitoring device(s) 146 can communicate with the information system 142 via a direct connection, or remotely through a network (not shown) that can include, for example, a LAN, a WAN, a WLAN, and/or the Internet.

In some examples, the patient data is made available for display on the computer device 144. A healthcare provider (e.g., a nurse and/or physician) can augment the patient data by inputting patient information that is also stored to the information system 144. More specifically, the healthcare provider can input patient information corresponding to a particular patient 150, which patient information can be stored to the patient record (e.g., EMR). As one example, a nurse can input nursing notes, which nursing notes can be stored to the patient record in the information system. Example patient information can include any non-physiological information corresponding to a patient (e.g., name, age, date-of-birth (DOB), gender).

As discussed above, each information system 142 stores patient data that can be collected from the patient monitoring devices 146, as well as additional patient information, that can include information that is input by a healthcare provider. The information system 144 communicates the patient data and/or the additional patient data to a data management system (DMS) 160. The DMS 160 can be provided as a server, or a virtual server, that runs server software components, and can include data storage including, for example, a database and/or flat files. In the example system architecture 100 of FIG. 1, each facility system 108, 110 includes a corresponding DMS 160. In such an arrangement, each information system 142 communicates patient data, and/or additional patient data to the DMS 160. Furthermore, and as discussed in further detail below, the DMS 160 can communicate ancillary information to the information system 142. Communication between the DMS 160 and the information system(s) 142 can be achieved via a direct connection, or remotely through a network (not shown) that can include, for example, a LAN, a WAN, a WLAN, and/or the Internet.

In some examples, a DMS 160 corresponding to a particular facility system can be remotely located from any of the facilities 140 of the facility system 108, 110, or can be located at a particular facility 140 of the facility system 108, 110. In the example system architecture 100 of FIG. 1, the DMS 160 is remotely located from either facility 140 within each of the facility systems 108, 110. It is contemplated, however, that the DMS 160 can be located at one of the facilities 140, and remote from the other facility 140.

In the example system architecture 200 of FIG. 2, a DMS 180 is provided that is common to (the same for) the facility systems 108, 110. For example, the DMS 180 can be described as being common to various facility systems 108, 110, and is not associated with a particular facility system 108, 110. For example, the DMS 180 can be hosted by a third-party vendor (e.g., a cloud service provider). In some examples, each information system 142 communicates with the DMS 180 via a direct connection, or remotely through a network (not shown) that can include, but is not limited to, a LAN, a WAN, a WLAN, and/or the Internet. In the example arrangement of FIG. 2, the DMS 180 communicates with each of the information systems 142 through the network 106. The information systems 142 communicate patient data and/or patient information to the DMS 180 and to the third party database 170. The DMS 180 can communicate ancillary information to the information system 142 and to the third party database 170, as discussed in further detail below.

In the example system architecture 100 of FIG. 1, the facility 140, or facility system 108, 110 installs the DMS 160 as a local DMS, and the DMS 160 sits at the local site with other servers that can include, for example, the information system 142. In some implementations, the DMS 160 can be sectioned off, or separated from a logical network perspective, but still physically exists with the other servers that belong to the respective facility 140. In some examples, server components are installed on the DMS 160, which components can include, for example, a database component, a database synchronization component, a web services component, and/or a structured query language (SQL) component. An information system interface can also be installed on the DMS 160, and functions as the interface to the information system 142. As one example, the information system interface can include OBLink, provided by GE Healthcare. In some implementations, the DMS 160 can be arranged in a multiple server configuration, in which one server only hosts web service related components and is logically segregated, and another server has the remaining necessary server components installed.

The example system architecture 200 of FIG. 2, provides for the remote location of data collection at the DMS 180. In such implementations, the DMS 180 can be provided at a third-party site, remote from any of the facilities 140, or facility systems 108, 110. The third-party functions as a DMS host, and the necessary server components are installed on the remotely hosted DMS 180. In some implementations, a business-to-business (B2B) virtual private network (VPN) can be created between the remotely hosted DMS 180 and the network of the facility 140 or facility system 108, 110. In this manner, the facility 140 and/or facility system 108, 110 forgoes the purchase and/or maintenance of another physical server, or DMS. Further, the up-time and the status of availability of the DMS 180 are easier to manage on the part of a dedicated third-party. The DMS' access to the network can be attended to by the third-party, as opposed to burdening the facility 140, or the facility systems 108, 110. Further, the third-party can implement virtual server technologies to leverage multiple DMS installations on a single physical server. In such implementations, a plurality of virtual servers are logically partitioned in a single physical server, and each virtual server has the capability of running its own operating system and server components, and can be independently booted.

In accordance with implementations of the present disclosure, the DMS 160 and/or 180 can synchronize and transfer data between the information systems 142, the third-party analysis system 170 and mobile devices 102. More specifically, the DMS 160, 180 processes and prepares the patient data and/or patient information for transfer to and storage at the third-party analysis system 170 or presentation on the mobile device 102, or multiple mobile devices 102, from the information system 142, and/or other systems, as discussed in further detail herein. The DMS 160, 180 also processes and prepares ancillary information for transfer to and storage in the information system 142 from the mobile device 102, or multiple mobile devices 102 for potential presentation at a corresponding computer device 144. Example DMSs can include, but are not limited to, the AirStrip Server provided by AirStrip Technologies, LLC, which AirStrip Server includes AirStrip Server Components installed therein.

Figure 3:
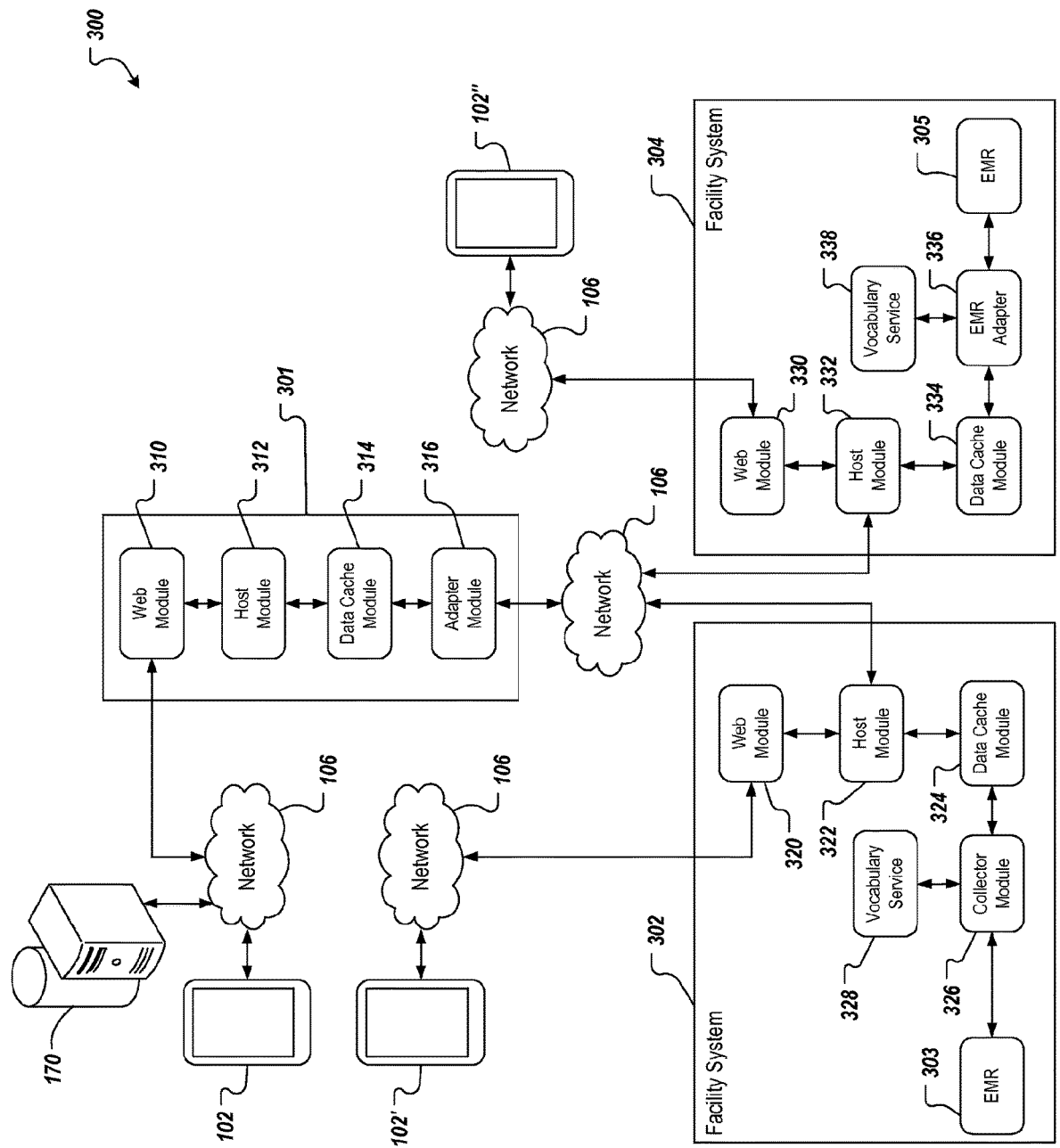
FIG. 3 is a functional block diagram of an example system in accordance with implementations of the present disclosure.
Figure 4:
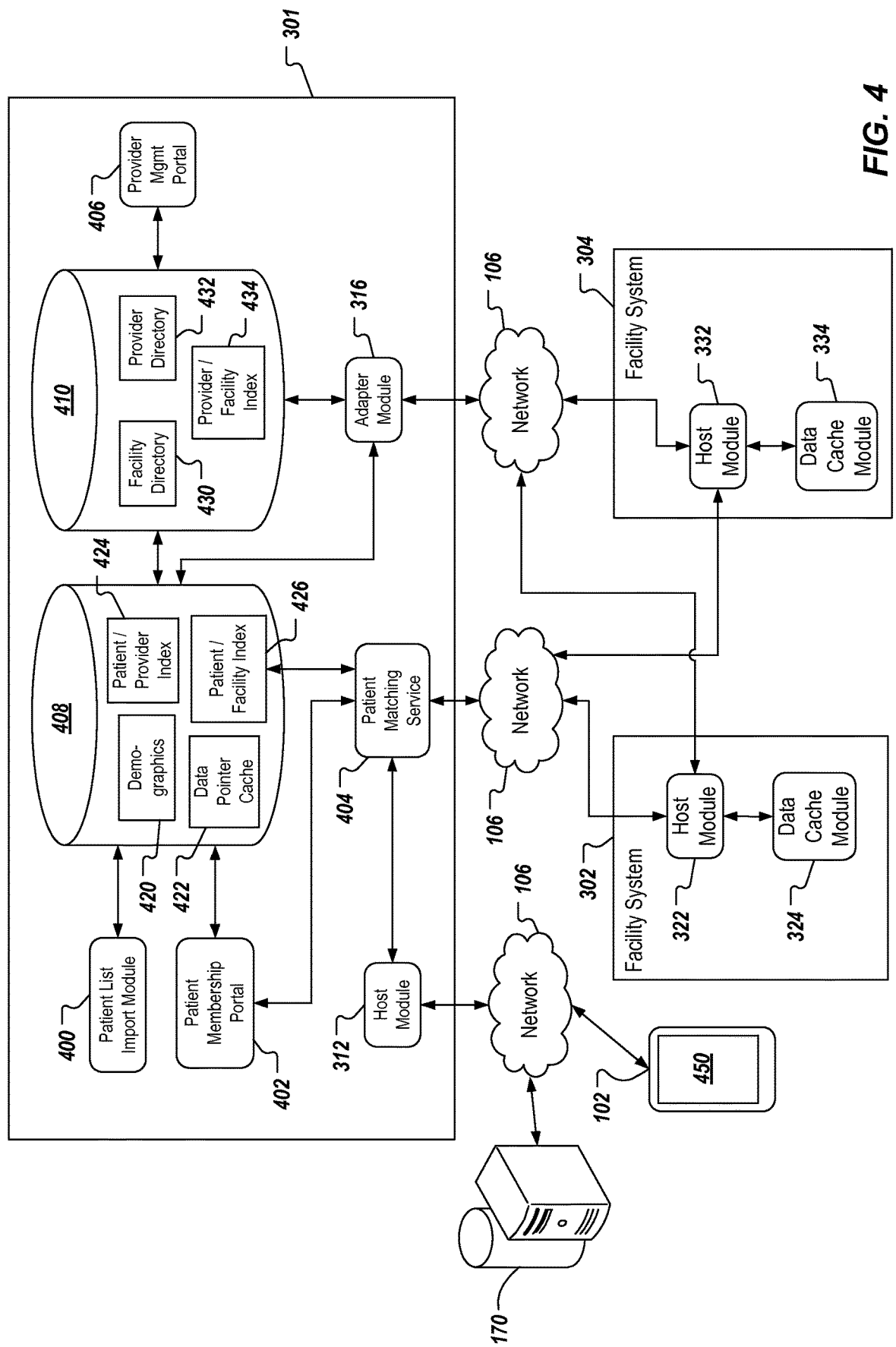
FIG. 4 is a more detailed view of the functional block diagram of FIG. 3.

Referring now to FIGS. 3 and 4, example module structure, or system 300 that can be implemented to provide features of the present disclosure will be described in detail. In some examples, the example system 300 enables patient data and patient information to be communicated to/from, and to be exchanged between mobile devices and data sources across healthcare continua. In some examples, each module can be provided as one or more computer-executable programs that are executed using one or more computing devices (e.g., computing devices provided as part of a DMS, computing devices located at one or more facilities of a facility system).

FIG. 3 illustrates an overview of the example system 300. In the depicted example, the module structure includes modules located at a federated platform 301 (also referred to as "platform" herein), a first facility system 302 and a second facility system 304. In some examples, the first facility system 302 and the second facility 304 can be included in at least a portion of a healthcare continuum, discussed in further detail herein. The facility system 302 includes a patient record module 303 (e.g., EMR module) that accesses one or more patient records managed and stored by the facility system 302. The facility system 304 includes a patient record module 305 (e.g., EMR module) that accesses one or more patient records managed and stored by the facility system 304.

In the depicted example, and as discussed in further detail herein, patient data and/or information can be provided for integrated and unified display on the mobile device 102 through the network 106 and the federated platform 301 from across healthcare continua (e.g., the facility systems 302, 304). In some examples, patient data and/or information can be provided for analysis to the third-party analysis system 170 and/or for display on a mobile device 102', 102" through the network 106 from a facility system (e.g., the facility system 302, 304). In some examples, the mobile devices 102, 102', 102" are the same device. That is, for example, a mobile device can receive patient data and/or information from across a healthcare continuum, and/or from individual facility systems.

In some implementations, the federated platform 301 includes a web module 310, a host module 312, a data cache module 314 and an adapter module 316, web module 320, a host module 322, a data cache module 324, a collector module 326. In general, modules of the federated platform 301 enable the federated platform 301 to retrieve and integrate data from multiple facility systems (e.g., the facility systems 302, 304) across healthcare continua. In some examples, the web module 310 provides a first-level network facing interface to the DMS infrastructure. In some examples, and in response to a request from a mobile device (e.g., the mobile device 102), the web module 310 performs request validation and user authentication and routes the request to the host module 312. In some examples, the web module 310 includes one or more sub-modules. Example sub-modules include a request validation sub-module, which validates received requests, a user authentication module, which authenticates an identity of the user and/or mobile device from which a request is received, and a request routing sub-module, which routes requests after validation and authentication.

In some implementations, the host module 312 orchestrates request processing. In some examples, the host module 312 includes one or more sub-modules. Example sub-modules include a request parsing sub-module that parses received requests, a pipeline assembly sub-module, a pipeline processing sub-module, an operation execution sub-module, a data access sub-module, a results formatting sub-module, an access control sub-module, an encryption sub-module, a data conditioning sub-module, and a logging sub-module. In some examples, the host module 312 parsers a received request (e.g., using the request parsing sub-module) to determine, for example, what type of device issued the request, which application executing on the device issued the request, and/or patient data/information (or other data such as analytical data, discussed below) is needed to fulfill the request. In some examples, and based on the parsed information, the host module 312 builds a pipeline (e.g., using the pipeline assembly sub-module). In some examples, a pipeline can be provided as a list of tasks that need to be executed to fulfill the request. Example tasks can include retrieving particular patient data/information, processing retrieved patient data to generate additional data and/or data visualizations (e.g., analytical data, trend graphs, discussed below), encrypting/decrypting retrieved data, performing access control to retrieve data, generating logs of tasks.

In some implementations, the host module 312 coordinates data retrieval with the data cache module 314 (e.g., using the data access sub-module). The retrieved data is provided back to the host module 312. In some examples, the host module 312 processes the retrieved data (e.g., using the operation execution sub-module, the results formatting sub-module and/or the data conditioning sub-module). In some examples, the retrieved data is processed to generate additional data (e.g., data used for data visualizations). In some examples, the retrieved data and/or the additional data are conditioned to provide efficient transfer back to the requesting mobile device. In some examples, conditioning can include converting data based on transmission protocol, formatting data for optimal display on the particular device, and/or packaging data to send to the requesting device.

In some implementations, the data cache module 314 enables access to and optional storage of detailed patient data/information used by other components of the system 300. In some examples, the data cache module 314 includes one or more sub-modules and/or data stores. An example sub-module can include a cache services sub-module. In some examples, the data cache module 314 can operate in a pass-through mode (real-time mode) and a reposed mode. In some examples, patient data/information required to satisfy a given request can be directly accessed from a source system (e.g., the facility system 302, 304) in real-time. In such examples, the data cache module 314 operates in a pass-through mode, retrieving the patient data/information from multiple data sources and passing the patient data/information onward for responding to the request. In some examples, an application program interface (API), or other programmatic mechanism can be used to retrieve the patient data/information. In some examples, in the pass-through mode, patient data/information is not stored in a persistent data store accessed by the data cache module 314. In some implementations, it might be desired to improve retrieval performance. Consequently, the data cache module 314 can store data identifiers and/or pointers in a persistent data store. When in the pass-through mode, the data cache module 314 uses the adapter module 316 to perform the actual retrieval of patient data/information from one or more facility systems.

In some examples, the patient data/information that is required to satisfy a request cannot be directly accessed from the facility systems (e.g., the facility systems 302, 304). In such examples, the data cache module 314 operates in the reposed mode. In some examples, in the reposed mode, the data cache module 314 stores a detailed copy of the patient data/information in the persistent data store. That is, for example, stored patient data/information is stored at the DMS-level, but had been retrieved from remote data sources (e.g., data sources located at the facility systems 302, 304). In some examples, when a request is made for patient data/information in the reposed mode, the patient data/information is retrieved directly from the persistent data store (e.g., by the cache services sub-module).

In some implementations, the adapter module 316 enables the retrieval of patient data/information from across healthcare continua. Consequently, the adapter module 316 can be referred to as a federated adapter module. In some examples, in response to receiving a request from the mobile device 102 for patient data/information from multiple data sources (e.g., the facility systems 302, 304), the data cache module 314 utilizes the adapter module 316 to retrieve the requested patient data/information from the multiple data sources. In some examples, the adapter module 316 communicates with local host modules (discussed in further detail below) of the respective facility systems.

In some implementations, the request processing operation of the federated platform 301 is stateless. More particularly, the modules of the federated platform 301 handle each received request as a distinct unit and, once a request is handled, stores no state information associated with a completed request. In other words, after the federated platform 301 has processed a request, the federated platform 301 (e.g., modules within the DMS 302 that handled the request) "forgets" that the request even occurred. In this manner, subsequently received requests are not influenced by (e.g., handled based on) previously processed requests.

In some examples, operation of the federated platform 301 is stateless, but the federated platform 301 can still provide a log of requests handled (e.g., using the logging sub-module). For example, a request log can be accessed during an audit of the system 300.

In some implementations, each facility system 302, 304 includes one or more local web modules 320, 330, one or more local host modules 322, 332, one or more local data cache modules 324, 334, and one or more vocabulary service modules 328, 338. In the depicted example, the facility system 302 includes one or more collector modules 326, and the facility system 304 includes one or more patient record (EMR) adapter modules 336.

In some examples, each of the web modules 320, 330 provides functionality as similarly discussed above with respect to the web module 310. More particularly, the web modules 320, 330 operate at a local level (e.g., local to the respective facility systems 302, 304), each performing request validation and user authentication, and routing requests to the respective local host modules 322, 332. For example, the web modules 320, 330 can receive requests from the respective mobile devices 102', 102", can validate the requests and authenticate the respective users/mobile devices, and route the requests accordingly. In some examples, each web module 320, 330 includes one or more sub-modules. Example sub-modules include a request validation sub-module, which validates received requests, a user authentication module, which authenticates an identity of the user and/or mobile device from which a request is received, and a request routing sub-module, which routes requests after validation and authentication.

In some examples, each of the local host modules 322, 332 provides functionality as similarly discussed above with respect to the host module 312. More particularly, the local host modules 322, 332 operate at a local level (e.g., local to the respective facility systems 302, 304), each orchestrating request processing. In some examples, the local host modules 322, 332 orchestrate request processing for requests received from the mobile device 102 through the federated platform 301, and/or from the respective mobile devices 102', 102" through the respective local web modules 320, 330. In some examples, each local host module 322, 332 includes one or more sub-modules. Example sub-modules include a request parsing sub-module that parses received requests, a pipeline assembly sub-module, a pipeline processing sub-module, an operation execution sub-module, a data access sub-module, an access control sub-module and an encryption sub-module.

In some examples, each of the local data cache modules 324, 334 provides functionality as similarly discussed above with respect to the data cache module 314. More particularly, the local data cache modules 324, 334 operate at a local level (e.g., local to the respective facility systems 302, 304), each enabling access to and optional storage of detailed patient data/information used by other components of the system 300. In some examples, the each data cache module 324, 334 can operate in a pass-through mode and a reposed mode, as discussed above with respect to the data cache module 314. In the pass-through mode, the local data cache modules 324, 334 retrieve the patient data/information from one or more local data sources and passed the patient data/information onward for responding to the request. In some examples, it might be desired to improve retrieval performance. Consequently, the local data cache modules 324, 334 can store data identifiers and/or pointers in a persistent data store. When in the pass-through mode, the local data cache modules 324, 334 use the collector module 326 and the patient record adapter module 336, respectively, to perform the actual retrieval of patient data/information from local data source(s) (e.g., the patient record module 303 and the patient record module 305, respectively). In some examples, when in the pass-through mode, the local data cache modules 324, 334 can write data back to the respective patient record modules 303, 305.

In some examples, the patient data/information that is required to satisfy a request (e.g., from the mobile device 102', 102") cannot be directly accessed from the local data sources (e.g., the patient record modules 303, 305). In such examples, each local data cache module 324, 334 can operate in the reposed mode. In some examples, in the reposed mode, the local data cache module 324, 334 stores a detailed copy of the patient data/information in the persistent data store. That is, for example, stored patient data/information is stored at the local level, having been previously received from local data source(s) (e.g., the patient record modules 303, 305). In some examples, when a request is made for patient data/information in the reposed mode, the patient data/information is retrieved directly from the persistent data store (e.g., by the cache services submodule).

In some implementations, the collector module 326 and the adapter module 336 are specific to the type of patient record module 303, 305, respectively. In the example of FIG. 3, the patient record module 303 can be accessed based on a particular messaging protocol. An example messaging protocol can include the Health Level 7 (HL7) messaging protocol. In some examples, patient data/information provided based on such messaging protocols is reposed by the data cache module 324. Consequently, requests for such data can be fulfilled based on operation of the data cache module 314 and/or the local data cache module 324 in the reposed mode, as discussed above. In some examples, changes to patient records in the patient record module 303 can trigger updating of reposed patient data/information by the data cache modules 314, 324. For example, the collector module 326 can automatically receive a message from the patient record module 303 in response to a change/updated, triggering updating/changing of reposed patient data/information.

In the example of FIG. 3, the patient record module 305 supports programmatic interface (e.g., API) access. In some examples, patient data/information provided through programmatic interfaces is passed-through the data cache module 314 and/or the data cache module 334. Consequently, requests for such data can be fulfilled based on operation of the data cache module 314 and/or the local data cache module 334 in the pass-through mode, as discussed above. In this manner, such patient data/information is not persisted by the data cache module 314, 334.

Although the example of FIG. 3 depicts facility systems 302, 304 having different types of patient record modules 303, 305, it is appreciated that facility systems can include any appropriate combination of types of patient record modules and any number of patient record modules (e.g., patient record modules 303, 305), and respective adapter modules (e.g., modules 326, 336). Further, although the example of FIG. 3 depicts two facility systems, implementations of the present disclosure are applicable in instances include any number of facility systems.

In some implementations, the vocabulary services modules 328, 338 perform translation between the vendor-specific vocabularies and a standard vocabulary. In this manner, patient data/information retrieved through the modules 303, 305 use standard vocabulary to be provided back to the third-party analysis system 170 and the mobile device 102 in a unified manner. For example, the patient record modules 303, 305 can each be provided by a respective third-party (e.g., a vendor) and can record data/information based on a vocabulary that is specific to the particular vendor. Consequently, data sources provided from different third-parties can refer to the same data/information or type of data/information using different terminology. In some examples, each vocabulary service module 328, 338 is specific to a respective patient record module 303, 305.

FIG. 4 is a more detailed view of the functional block diagram of FIG. 3, depicting additional components of the example system 300. In the depicted example, the federated platform 301 further includes a patient list import module 400, a patient membership portal module 402, a patient matching service module 404, a provider management (mgmt) module 406, a patient information data store 408, and a directory information data store 410. In some examples, the patient information data store 408 stores patient demographic information 420, a data pointer cache 422, a patient-to-provider index 424 and a patient-to-facility index 426. In some examples, the directory information data store 410 stores a facility directory 430, a provider directory 432, and provider-to-facility index 434.

In some implementations, the patient list import module 400 enables initial and ongoing import of patient lists and patient demographic information for patients. In some examples, the patient list import module 400 provides an interface to receive a patient list, e.g., provided in a computer-readable document, and processes the patient list to populate the patient information data store 408 (e.g., the demographic information 420). In some examples, the patient membership portal module 402 provides an interface that enables users (e.g., an administrator) to establish relationships between patient data/information stored across healthcare continua and particular patients. In some examples, healthcare providers, facilities and/or facility systems across healthcare continua can be included in a healthcare organization (e.g., an accountable care organization (ACO)). In some examples, the patient membership portal module 402 enables a user to define relationships between multiple patient records (e.g., based on respective medical record numbers (MRNs)) to the healthcare organization. In some examples, relationship information defined through the patient membership portal module 402 can be stored in the patient information data store 408.

In some implementations, the patient matching service module 404 can be accessed by the host module 312 and the patient membership portal module 402. In some examples, the patient matching service module 404 can be accessed by an application executed on a mobile device (e.g., the mobile device 102) through the host module 312. In some examples, the patient matching service module 404 processes patient data and/or patient information to identify potential patient matches between disparate data sources (e.g., multiple, different EMRs across the healthcare continuum). In some examples, patient information associated with confirmed matches (e.g., confirmed by an administrator through the patient membership portal module 402, confirmed by a healthcare provider using a mobile device through the host module 312) can be stored in the patient information data store 408. In some examples, a patient matching user interface (UI) is provided (e.g., displayed on a mobile device) and can be used by a healthcare provider to search for patients and establish, record and/or confirm relationships between patient records in different systems that are related to a single patient.

In some examples, the demographics information 420 includes information that can be used to identify any patient that has been established in the system. In some examples, the demographics information 420 can be used to search for patients, discussed in further detail herein. Example demographics information can include name, age and/or gender. In some examples, the data pointer cache 422 stores identifiers associated with detailed patient data. In some examples, the identifiers point to particular data stores, in which to be retrieved patient data/information is stored. In this manner, retrieval performance (e.g., speed) can be improved. In some examples, the patient-to-provider index 424 maps particular patients to one or more healthcare providers, and/or particular healthcare providers to one or more patients. For example, a patient can be treated by a plurality of healthcare providers (e.g., members of a patient care team, discussed below). As another example, a healthcare provider can treat a plurality of patients. In some examples, the patient-to-facility index 426 maps particular patients to one or more facilities and/or facility systems. In some examples, a patient can be mapped to particular facilities based on respective MRNs of the patient at the respective facilities. For example, a healthcare continuum for a particular patient can include a hospital and a clinic. In this example, the patient-to-facility index can map the patient to the MRN of the hospital and the MRN of the clinic.

In some implementations, the provider management portal module 406 provides an interface (e.g., web portal) to enable members of a healthcare organization (e.g., ACO) to update healthcare provider directory information and/or healthcare provider-to-facility relationships. For example, a physician can be associated with one or more facility systems of the healthcare organization and credentials (e.g., for log on and/or authentication) can be provided to enable the physician to access patient data/information provided from the one or more facility systems.

In some examples, the facility directory 430 provides a directory of the facilities interfaced to by the system (e.g., the federated platform 301). In some examples, the facility directory 430 also provides configuration parameters to enable communication (messaging) between the system and computing devices associated with the respective facilities. In some examples, the provider directory 432 includes a directory of healthcare providers (e.g., nurses, physicians, specialists, and the like) that are able to access patient data/information through the system (e.g., the federated platform 301). In some examples, the provider-to-facility index 434 maps each healthcare provider (e.g., in the provider directory) to one or more facilities. For example, a healthcare provider can treat patients at multiple facilities. In some examples, the provider-to-facility index 434 securely stores credentials of healthcare providers for facilities that the healthcare provider is mapped to. For example, a healthcare provider can have first credentials for accessing patient data/information at a first facility, and can have second credentials for accessing patient data/information at a second facility. In some examples, the provider-to-facility index 434 supports single sign-on functionality discussed in further detail herein.

An example data flow will be discussed to illustrate implementations of the present disclosure. It is appreciated that implementations of the present disclosure are equally applicable to other data flows. The example data flow can be initiated in response to a request received from a mobile device (e.g., the mobile device 102). In some examples, the request includes a user identifier, a device identifier, a patient identifier, patient data identifiers, patient information identifiers and additional data identifiers. In some examples, the user identifier can be used to determine the particular user that has issued the request, and the device identifier can be used to determine the particular device that transmitted the request. In some examples, the patient identifier identifies the particular patient that is the subject of the request, the patient data identifiers identify the particular patient data that has been requested, the patient information identifiers identify the particular patient information that has been requested, and the additional data identifiers identify additional data that has been requested. For example, the patient data identifiers can indicate that patient vital data has been requested, and the additional data identifiers can indicate that vitals alarm data and vital data trend visualizations have also been requested.

In the example data flow, the web module 310 receives the request and processes the request to validate the request and to authenticate the user, who submitted the request (e.g., based on the user identifier and/or the device identifier). Upon validation and authentication, the web module 310 provides the request to the host module 312. The host module 312 processes the request, as discussed above. In some examples, it can be determined that patient data/information required to fulfill the request can be provided from the data cache module 314 (e.g., reposed mode). In such examples, the patient data/information is provided to the host module 312 from the data cache module 314. In some examples, it can be determined that that patient data/information required to fulfill the request is to be retrieved from one or more data sources across a healthcare continuum of the patient (e.g., federated mode).

In some examples, if patient data/information required to fulfill the request is to be retrieved from one or more data sources across the healthcare continuum (e.g. federated mode), request information (e.g., assembled by the host module 312, as discussed above) is provided to the adapter module 316 by data cache module 314. In some examples, the adapter module 316 accesses information stored in the directory store 410 to request data from one or more facility systems (e.g., the facility system 304). For example, the adapter module 316 can be aware of which facility systems to retrieve patient data/information from (e.g., based on the patient-to-facility index 426) and can access the provider-to-facility index 434 to retrieve user credentials for the particular provider (e.g., user that issued the request). In this manner, the adapter module 316 can provide appropriate user credentials to respective facility systems for patient data/information retrieval.

In some examples, the adapter module 316 sends requests to identified facility systems, each request identifying patient data/information and providing appropriate user credentials. In some examples, respective host modules (e.g., the host module 332) of the facility systems receive the requests from the adapter module 316, and can process the requests as similarly discussed above with reference to the host module 312. The respective host modules fulfill the requests and provide the requested patient data/information back to the adapter module 316. In some examples, the adapter module 316 provides the retrieved patient data/information to the host module 312, which completes processing of the request, as discussed above, and provides a response to the mobile device that issued the request.

As discussed at the outset, the present disclosure provides integrated data to the third-party analysis system 170 and to a healthcare provider, or user of the mobile device 102, with secure, remote access to patient data and/or patient information. Example patient data can include physiological data. In some examples, physiological data can be obtained from patient monitoring device(s). In some examples, physiological data can be obtained by a local healthcare provider (e.g., a nurse, or physician measuring blood pressure, temperature, heart rate). In some examples, physiological data can be recorded in one or more patient records (e.g., EMRs). In the example case of a maternity patient, patient data can include delivery progress information such as cervical exam status, membrane status, gravida, para, epidural status, and/or whether the patient is attempting a vaginal birth after cesarean (VBAC). In some examples, the term patient information refers to information corresponding to a particular patient that is, for example, input into the information system 142 by the local healthcare provider. Example patient information can include the patient's name, the name of the doctor(s) assigned to the patient, the nurse(s) assigned to the patient, a facility identification, a patient bed identification, a summary of patient data, and/or chart annotations. The term patient information can also refer to patient information provided from one or more patient records (e.g., EMRs).

The patient data and/or patient information provided to the remotely located user can be provided as real-time data, and/or as historical data and information. The patient data and/or patient information is communicated between the mobile device 102 and the DMS 160, 180 using a secure connection that is established over the network 106. A secure log-in, or sign-on process is provided, which is preferably compliant with the provisions of the Health Insurance Portability and Accountability Act (HIPAA). The secure sign-on authenticates the identity of the user of the mobile device 102 based on a unique user ID and password combination. Both the user ID and the password must be correct in order to establish the secure communication between the mobile device 102 and the DMS 160, 180.

In some examples, a census, or patient list is provided, which captures a variety of the information and/or data described herein that is associated with each of one or more monitored patients 150. Strip charting is also provided, in which patient data and/or information can be presented to the user in graphical form. In the example case of a maternity patient, a fetal strip and maternal contraction information can be provided for a particular patient 150. More specifically, the particular patient 150 is selected from the patient list, and the patient information and/or data is subsequently presented. The presented information and/or data can include a fetal strip and maternal contraction waveform, the patient name, the hospital name, the patient room and/or bed number, and the date and time. The strip charting can provide a real-time view of the patient data, as well as a historical view of the patient data. More specifically, the waveform display can be updated in real-time, such that the user of the mobile device 102 observes the patient data as it occurs and/or is recorded. The user can scroll through the waveform display, to view historical patient data, as described in further detail below.

Several navigation features can be provided that enable the user to manipulate a view of the waveform display. In some implementations, the user can zoom in/out of the displayed image. In this manner, the user can view very specific waveform information, and/or other waveform micro-characteristics by zooming in, for example, and/or can view patterns or other waveform macro-characteristics by zooming out, for example. In some implementations, the user can scroll forward or backward through the waveform display. In this manner, the user can view historical patient data.

A patient data display can also be provided. In some implementations, the patient data display can overlay the strip charting described herein. In other implementation, the patient data display can be provided as an overlay, and/or as a separate display. The patient data display can include, but is not limited to, the patient's name, age, fetal gestation, gravida, parity, cervical exam information, and physician name.

Implementations of the present disclosure can be realized on any one of a number of operating systems, or platforms 302 associated with the particular mobile device 102. Example platforms include, but are not limited to, RIM Blackberry, Apple iOS and/or OS X, MS Pocket PC, Win Mobile (Pocket PC, Smartphone), Win Mobile (standard, professional) and/or any other appropriate platforms (e.g., Google Android, and Hewlett-Packard WebOS, Microsoft Windows, Unix, Linux).

As discussed in detail herein, implementations of the present disclosure are directed to systems and methods of providing integrated and unified views of patient data and patient information from disparate data sources and/or products. More particularly, implementations of the present disclosure provide integrated and unified views of patient data and patient information retrieved from across a healthcare continuum. In some examples, the healthcare continuum can include a plurality of disparate clinical data sources. In some examples, a clinical data source can correspond to one or more categories of healthcare services. Example categories can include emergency medical services (EMS), outpatient services, inpatient services, ambulatory services, post-acute services, home services and stand-alone services. Example EMS can include emergency departments (e.g., emergency room (ER) of a hospital), urgent care facilities and transport (e.g., ambulance). Example outpatient services and/or inpatient services can include hospitals and/or critical access hospitals (CAHs). Example ambulatory services can include clinics, physicians groups/offices, surgery centers and pre-acute care. Example post-acute services can include skilled nursing facilities, long-term care hospitals, rehabilitation centers and home healthcare. Example stand-alone services can include imaging centers (e.g., MIR), oncology centers, laboratories, virtual call centers and retail clinics.

As introduced above, implementations of the present disclosure are also directed to a platform (e.g., the federated platform 301) and service that enable pre-identified data to flow serially out of the platform in near-real-time, as new data or changes to existing data occur on a source system, a monitor, a sensor, and/or any other appropriate source of data that communicates with the platform. In some implementations, the platform is provided as the enterprise scalable, data- and vendor-agnostic mobility architecture, described herein, which processes and securely delivers patient data and information from medical devices, electronic medical records (EMRs) and patient monitors to third-parties (e.g., the third-party analysis system 170, which can process received data to perform one or more analytic determinations). In some examples, implementations of the present disclosure provide integration, filtering and unification of structured patient data and patient information from a plurality of data sources across healthcare continua.

Figure 5:
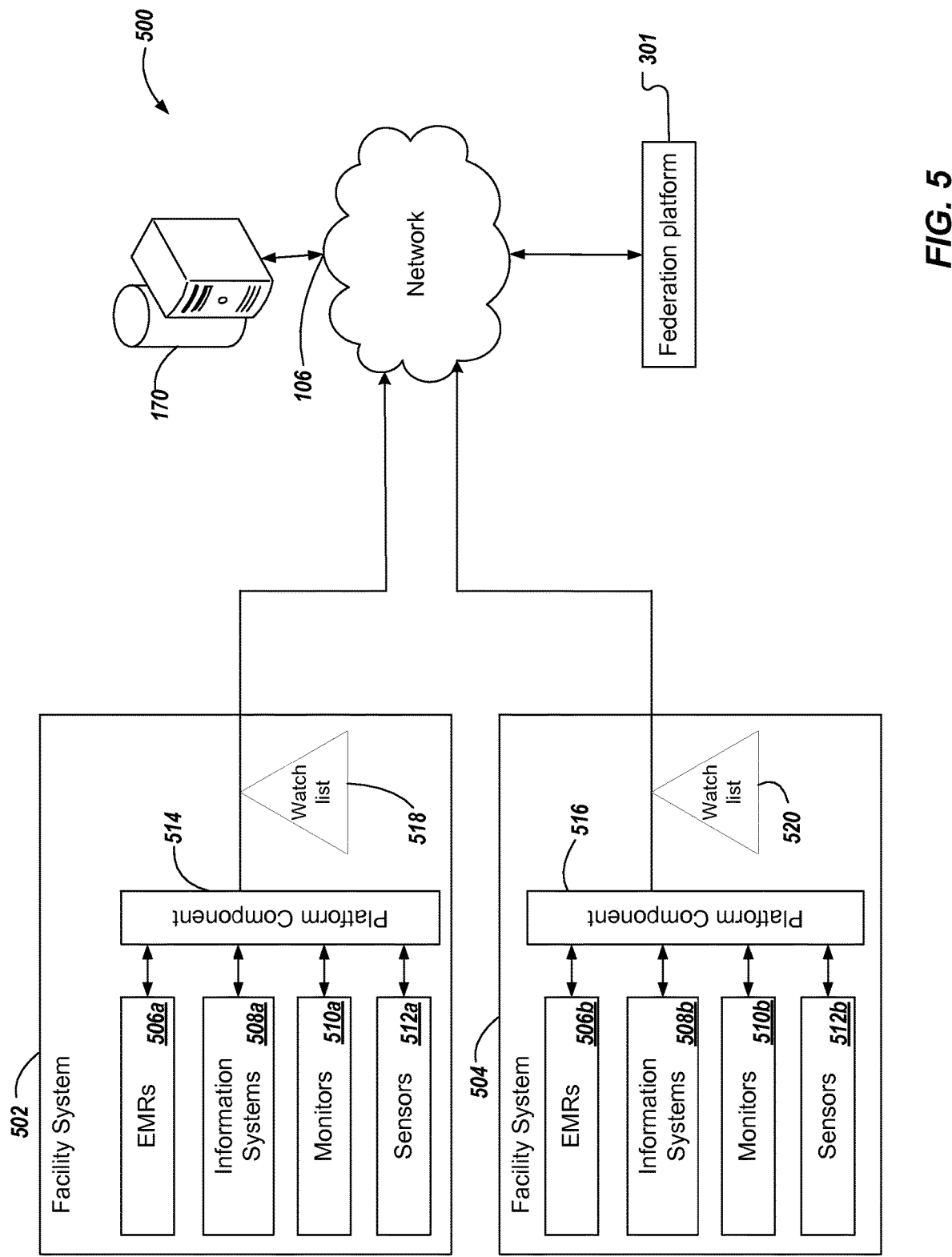
FIG. 5 is a functional block diagram of another example system in accordance with implementations of the present disclosure.

FIG. 5 depicts an overview of an example system 500. The example system 500 can include a plurality of facility systems that form a healthcare continuum. In the illustrated example, the system 500 includes a first facility system 502, a second facility system 504, the federated platform 301, and the third-party analysis system 170. As described in further detail herein, data is transferred from each of the first and second facility systems 502, 504 through the network 106 and federated platform 301 for analysis at the third-party analysis system 170. In some examples, the federated platform 301 is provided by one or more server systems (e.g., the DMS 180 of FIG. 2).

Although two facility systems are illustrated, implementations of the present disclosure can include one or more facility systems. Each facility system 502, 504 can include a plurality of data sources, a platform component 514, 516 and one or more watchlists 518, 520.

In the example of FIG. 5, example data sources for the respective facilities 502, 504 include EMR modules 506a, 506b, information systems 508a, 508b, patient monitors 510a, 510b, sensors 512a, 512b and/or any other appropriate devices or instruments that collect and transmit patient data. The data sources can provide patient data, medical alerts and/or alarm signals. For example, the facility system 502 can include an EMR module 506a, an information system 508a, a plurality of patient monitors 510a, sensors 512a and/or other devices or instruments that collect and transmit patient data. The facility system 504 can include an EMR module 506b, an information system 508b, a plurality of patient monitors 510b, sensors 512b and/or other devices or instruments that collect and transmit patient data.

As discussed in further detail herein, patient data and patient information can be provided from one or more disparate patient data sources (e.g., examples depicted in FIG. 5). A patient can be associated with one or more healthcare services across the healthcare continuum. For healthcare services provided across the healthcare continuum, the patient data and patient information can be distributed across the healthcare continuum. For example, a patient can be taken to a hospital by EMS (e.g., ambulance), can be treated in an emergency department of the hospital (e.g., ER), can stay in the hospital on an inpatient basis, can frequent a rehabilitation center (e.g., physical therapy), can be undergoing home healthcare (e.g., home nursing care), and patient samples can be sent to a laboratory for analysis (e.g., blood analysis provided by an external laboratory). In this example, treatment of the particular patient touches multiple facilities across the healthcare continuum, and each facility can generate its own patient data, patient information and patient records (EMRs 506a, 506b).

In general, an EMR 506a, 506b can be described as a digital medical record provided as an electronic document that can be processed (e.g., read from/written to) by one or more computer programs executed by one or more computing devices. Further, each entity or organization (e.g., clinic, hospital, physician, rehabilitation center, laboratory) that treats a patient can include its own, stand-alone information system that provides an EMR 506a, 506b that is specific to the information system. Consequently, multiple, disparate EMRs 506a, 506b can be provided for a single patient across the healthcare continuum. Within the context of the example above, a first EMR can be provided for the patient by an ambulance service that transported the patient to the hospital, a second EMR can be provided for the patient by the hospital, a third EMR can be provided for the patient by the rehabilitation center and a fourth EMR can be provided for the patient by a nursing company that is providing home nursing care to the patient. In some examples, and as noted above, EMRs can be generated from disparate information systems. Consequently, format and syntax of one EMR can be different from the format and syntax of another EMR.

In some examples, historical patient data and information can be provided for viewing by a healthcare provider, as well as providing real-time patient data for viewing to the healthcare provider. Extending the example above, the patient can be re-admitted to the hospital on an inpatient basis and can be connected to one or more patient monitoring devices that generate patient physiological data based on patient physiological activity. In accordance with implementations of the present disclosure, and as discussed in further detail herein, patient data and information from one or more of the first EMR, the second EMR, a third EMR or a fourth EMR, as well as real-time patient data can be provided for display to a healthcare provider (e.g., a physician attending to the patient) on a mobile device in an integrated and unified manner. For example, real-time and/or historical patient physiological data can be provided for analysis at the third-party analysis system 170. Implementations of the present disclosure enable integration and unification of the patient data across the products before sending to the third-party analysis system 170.

In some implementations, EMRs 506a, 506b access one or more patient records managed and stored by the facility systems 502, 504, respectively. The information systems 508a, 508b can provide data related to the facility systems 502, 504, respectively. The patient monitors 510a, 510b, sensors 512a, 512b and any other appropriate devices or instruments that collect patient data can be specific to a particular facility system. For example, a facility system corresponding to a cardiology department can include monitors, sensors and the other devices or instruments that support cardiac diagnosis and treatment.

In some implementations, the data platforms 514, 516 can receive and pull data from each of the data sources included in the corresponding facility system 502, 504, respectively. The data platforms 514, 516 can process the patient data by structurally mapping the data source information to a domain model. In accordance with implementations of the present disclosure, the domain model is a representation of a data structure for data that is to be processed by a third-party analysis system. In some examples, the domain model provides two or more sections that can be related to each other. For example, the sections can include a medication section, an order section, a diagnosis section, a treatment plan section and other patient related sections.

The domain model can be expanded or modified by adding or deleting one or more sections of the domain model to match any transformation of a third party database to which patient data/information is to be transferred. In some implementations, the domain model can be a source-agnostic domain model that enables interoperability among various systems. The mapping can enable one or more source-agnostic medical services. The mapping can also enable the display of the source data on a mobile application.

In some examples, the platform components 514, 516 can include adapters (e.g., provided as computer-executable programs) that are notified when new patient data has been collected by a data source or a change related to patient data has been recorded within a data source. In some examples, the platform components 514, 516 are components of the federated platform 301. In response to a notification, a platform component 514, 516 receives the data and maps the data to the domain model. In this manner, a populated data structure can be provided in response to a notification. As described herein, the populated data structure can be used by the federated platform 301 to transmit patient data to and to display patient data on one or more devices (e.g., the mobile device 102). As also described herein, the populated data model can be used to provide data to the third-party analysis system 170.

In some implementations, each watchlist 518, 520 defines data elements in the data sources that are to be provided to the third-party analysis system 170 (e.g., in response to a change (add, delete, modify)). In some examples, and as described in further detail herein, a watchlist 518, 520 can review a populated data structure to determine the present of changed data that is to be transmitted to the third-party analysis system 170.

The platform components 514, 516 can establish a connection with the third-party analysis system 170 over the network 106. If the connection is closed, the platform components 514, 516 can reestablish the connection with the third-party analysis system 170. The watchlists 518, 520 can be used to perform a security check of the network 106 connection and of the third-party analysis system 170. The security check can include an identification of the IP address and TCP port number of the third-party analysis system 170 to determine whether the third-party analysis system is "approved" for receiving patient data (e.g., is white-listed). For example, and as described herein, the watchlists 518, 520 can provide connection information associated with a respective third-party system, which information can be used to determine whether the third-party system is allowed to receive data.

If the platform components 514, 516 have data to send to the third-party analysis system 170 and the connection is not established (e.g., the identification failed), the platform components 514, 516 can a queuing mode. In some examples, the queuing mode can use disk resources on the server, on which the platform components 514, 516 are running, to await establishment of the connection. In some examples, if the connection remains continuously unavailable for prolonged periods of time, the queue can become full and as a result, streaming data can be discarded without being sent. After the connection is reestablished, the queued data can be transmitted and the platform components 514, 516 can switch from a queuing mode to a normal operation mode. Patient data is sent to the platform components 514, 516 in chronological order regardless of the mode of the platform components 514, 516, unless the queue becomes full. In some examples, the platform components 514, 516 can also include a secure messaging function that embodies an encryption of the patient data to be streamed.

In some implementations, the output of the platform components 514, 516 is in the form of a populated data structure that includes an event header and an event. An example populated structure is provided as:

```
internal class EventHeader
{
    internal string mode;
        //Export or Stream.
    internal string topic;
        internal string dataSource;
        internal string eventType;
            //Document, Laboratories, Vitals, Diagnosis,
Problems, PMEvents, PMWaves, ECGStatements, ECGWaves,
SecureMsg, Audit...
        internal string sourceID;
        internal string standardVocab;
    //LOINC, SNOMED-CT, ICD9, ICD10, RXNORM...
        internal string standardID;
        internal string patientMRN;
}
```

In some examples, the event header can be followed by the event itself, which includes data that can vary based on the event type. For example, if the event type is a "LabResult" or "Vitals," the respective events can be provided as:

```
internal class LabEvent
{
    public string Name;
    public DateTimeOffset ReportedTime;
    public List<LaboratoryObservation> Observations;
    public IEnumerable<string> Notes;
    public string OrderId;
    public long CollatingSequence;
    public long MainCategoryCollatingSequence;
}
internal class ObservationEvent
{
    public double Id;
    public string Name;
    public string Value;
    public string UnitsOfMeasure;
    public string Normalcy;
    public string ReferenceRange;
    public DateTimeOffset ObservedTime;
    public string Status;
    public string Facility;
    public string ConditionOfSpecimen;
    public long CollatingSequence;
}
```

In some implementations, the third-party analysis system 170 receives an initial "full export" of past events prior to activating the transmission of current data to the third-party analysis system 170. In this manner, the third-party analysis system 170 is seeded with all events and associated patient data prior to being activated for near-real-time receipt of changing patient data. In some examples, the platform components 514, 516 can manually triggered (e.g., by a user) to perform the export of past data. In some examples, the export process can be throttled to prevent excessive loading of a data source (e.g., EMR module 506a, 506b, an information system 508a, 508b, a monitor 510a, 510b, sensors 512a, 512b and/or other devices or instruments that collect and transmit patient data). In some examples, a type of throttling can depend on the data source type. In some implementations, the platform components 514, 516 do not export the data in the sequence in which they occurred. The export of data can depend on the data source capabilities. For example, the export can be performed one data source type at a time, such as after exporting data from all EMRs, then all waveforms are exported.

In some examples, a full export can be performed by using one or more watchlists 518, 520. For example, the watchlists 518, 520 can be used to filter the data streamed by the platform components 514, 516 by defining (identifying), which data is to be streamed in response to a change. In some examples, the filtering process performed by the watchlists 518, 520 is based on semantic mapping, as described in detail with reference to FIG. 6. The patient data and/or patient information filtered by the watchlists 518, 520 is streamed to the third-party analysis system 170 and/or the federated platform 301 over the network 106. In some examples, the federated platform 301 can integrate the incoming patient data and/or patient information into a single federated feed by connecting to the third-party analysis system 170.

In some implementations, the platform components 514, 516 have multiple transmission modes. The transmission mode corresponding to past data can be set to "export." The transmission mode corresponding to near-real-time data can be set to "stream." The transmission can be performed using a connection protocol or a compressed text file (e.g., a Java Script Object Notation (JSON)) generated, compressed, and transmitted to the third-party analysis system 170. In some examples, the export mode includes manually triggered export of past data stored in respective data sources. In some examples, the stream mode includes streaming of events and patient data in near-real-time. In some examples, near-real-time describes actions that can be automatically executed, without requiring human input and without any intentional delay, taking into account the processing limitations of the systems involved (e.g., computing devices hosting and/or executing the data sources, the platform components, the watchlists, etc.) and any time required to process data. More particularly, and in response to an event (e.g., changed patient data identified on a watchlist), a populated data structure and/or portions of the populated data structure can be transmitted to the third-party analysis system 170).

In some implementations, EMRs 506a, 506b or other data sources can undergo configuration changes to provide observations, lab results, documents, etc. in a different format. The platform components 514, 516 can detect the changes of the data source structure (e.g., a row of a nursing Flowsheet can be added or deleted). The detected change can generate an administrative alert that is automatically transmitted to a support team and/or a site's administrator, who can determine whether the data source change affects the unified data to be stored at the third-party analysis system 170.

Figure 6:
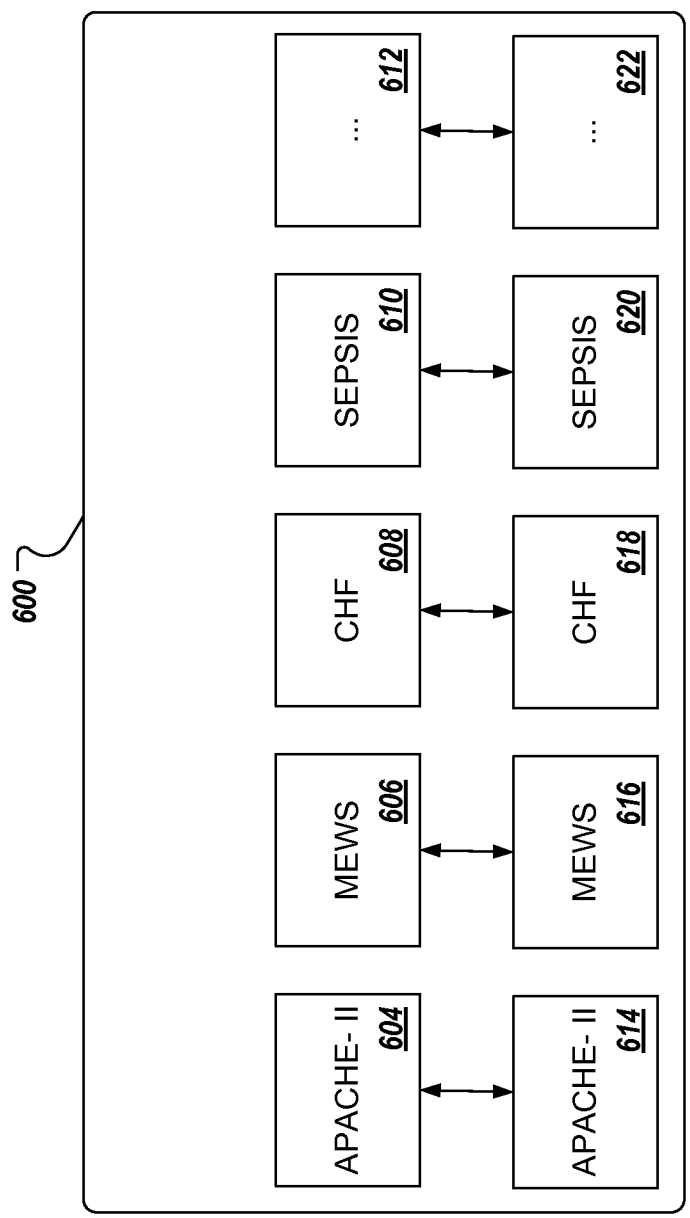
FIG. 6 depicts a representation of a watchlist in accordance with implementations of the present disclosure.

FIG. 6 depicts a representation of an example watchlist 600. In some examples, the watchlist 600 is provided for selective execution of a streaming function. In some examples, each facility can include one or more watchlists 600, each watchlist corresponding to particular data and/or events, for which streaming is to be executed. In some examples, the watchlist 600 is provided for a particular third-party analysis system, to which data and/or events are to be streamed. For example, the watchlist 600 can include the IP address and TCP port number for the third-party analysis system, to which the events and/or data are to be streamed. In some examples, the watchlist 600 is provided as a computer-readable file.

In some implementations, the watchlist 600 provides a list of topics that are to be monitored for a particular facility. Example topics can include a clinical score, a measure, a condition, and/or other higher order concepts that define an issue being addressed by watching data elements corresponding to a particular topic. Accordingly, the watchlist 600 includes topics, and one or more data elements associated with a respective topic. In the example of FIG. 6, example topics include an Acute Physiology and Chronic Health Evaluation II (APACHE-II) score 604, a modified early warning (MEW) score 606, congestive heart failure (CHF) 608, SEPSIS 610 and one or more other topics 612. In some examples, the APACHE-II score is provided as an integer score that indicates a severity of disease and/or risk of death. In some examples, the MEW score indicates a degree of illness of a patient, and is based on physiological data (e.g., systolic blood pressure, heart rate, respiratory rate, body temperature) and observational information (e.g., level of consciousness, AVPU).

In some implementations, and for each topic and for each data source, the watchlist 600 indicates one or more data elements (a list of data elements) that are to be streamed when the data element changes in a respective data source. Accordingly, in the depicted example, the APACHE-II score 604 corresponds to APACHE-II score data elements 614, the MEW score 606 corresponds to MEW score data elements 616, CHF 608 corresponds to CHF data elements 618, SEPSIS 610 corresponds to SEPSIS data elements 620, and any other topics 612 corresponds to respective data elements 622. In some examples, and for each data element 614, 616, 618, 620, 622, the watchlist 600 provides a standard identifier. In some examples, the standard identifiers are sent as part of the stream, such that respective data elements can be identified by the third-party analysis system based on respective standard identifiers.

In some implementations, each of the data elements 614, 616, 618, 620, 622 can be configured as a tuple (e.g., a quadruplet). In some examples, the form of the tuple can include a name, a data source, a source ID and a standard ID (e.g., [Name, Date_Source, SourceID, StandardID]). In some examples, the tuple further includes a value (V) of the respective data element and/or a time (T), at which the value was generated (e.g., by a monitor, by a sensor). The name can be a human-readable name for the data element (e.g., as opposed to machine-readable byte code). The data source can indicate the particular data source and/or type of data source (e.g., EMR module, information system, monitor, sensors), from which a value of the data element is provided. For example, in the case of a monitor as the data source (e.g., heart rate monitor), the Data_Source value of the respective tuple can be provided as "Patient Monitor Waveforms," "Patient Monitor Parameters," or "Patient Monitor Events" to indicate the modality (e.g., waveform, value, event (alert)). As another example, in the case of ECG data sources, the Data_Source value of the respective tuple can be provided as "ECG waveform" or "ECG diagnosis" to indicate the modality.

The source ID can be an identifier for the data source that is provided in the nomenclature of the particular data source. For example, an EMR provided by a first vendor can use a first source ID (name) for a particular type of data element, and an EMR provided by a second vendor can use a second source ID, that is different from the first source ID, for the particulate type of data element. That is, the same type of data element can be assigned different source IDs. The standard ID can be the identifier for the data element using an applicable healthcare standard vocabulary. In this manner, different source IDs can be mapped to a common standard ID. Continuing with the example above, the first source ID can be provided in a first tuple with a standard ID, and the second source ID can be provided in a second tuple with the standard ID. In this manner, although the first source ID and the second source ID are different, they both map to the same standard ID.

Example standard IDs can include a Logical Observation Identifiers Names and Codes (LOINC) identifier, a Systematized Nomenclature of Medicine—Clinical Terms (SNOMED-CT) identifier, an International Classification of Diseases (ICD) identifier (e.g., ICD-9, ICD-10), and a Current Procedural Terminology (CPT) identifier (e.g., CPT-4). In some examples, the standard ID is used to identify the data element when sending information to a third-party system (e.g., the third-party analysis system 170 in FIG. 1). The standard ID can indicate the clinical concept by denoting the representation of the data source for each data element to the third-party system.

In some implementations, a tuple for a particular data element can be provided in multiple topics. For example, and as described above, each topic can include a clinical score, a measure, a condition, and/or other higher order concepts that define an issue being addressed. Accordingly, a particular data element (e.g., heart rate) can be used in determining both a first topic and a second topic. In some examples, a data element (i.e., a data element tuple) is provided only once for each topic.

Figure 7:
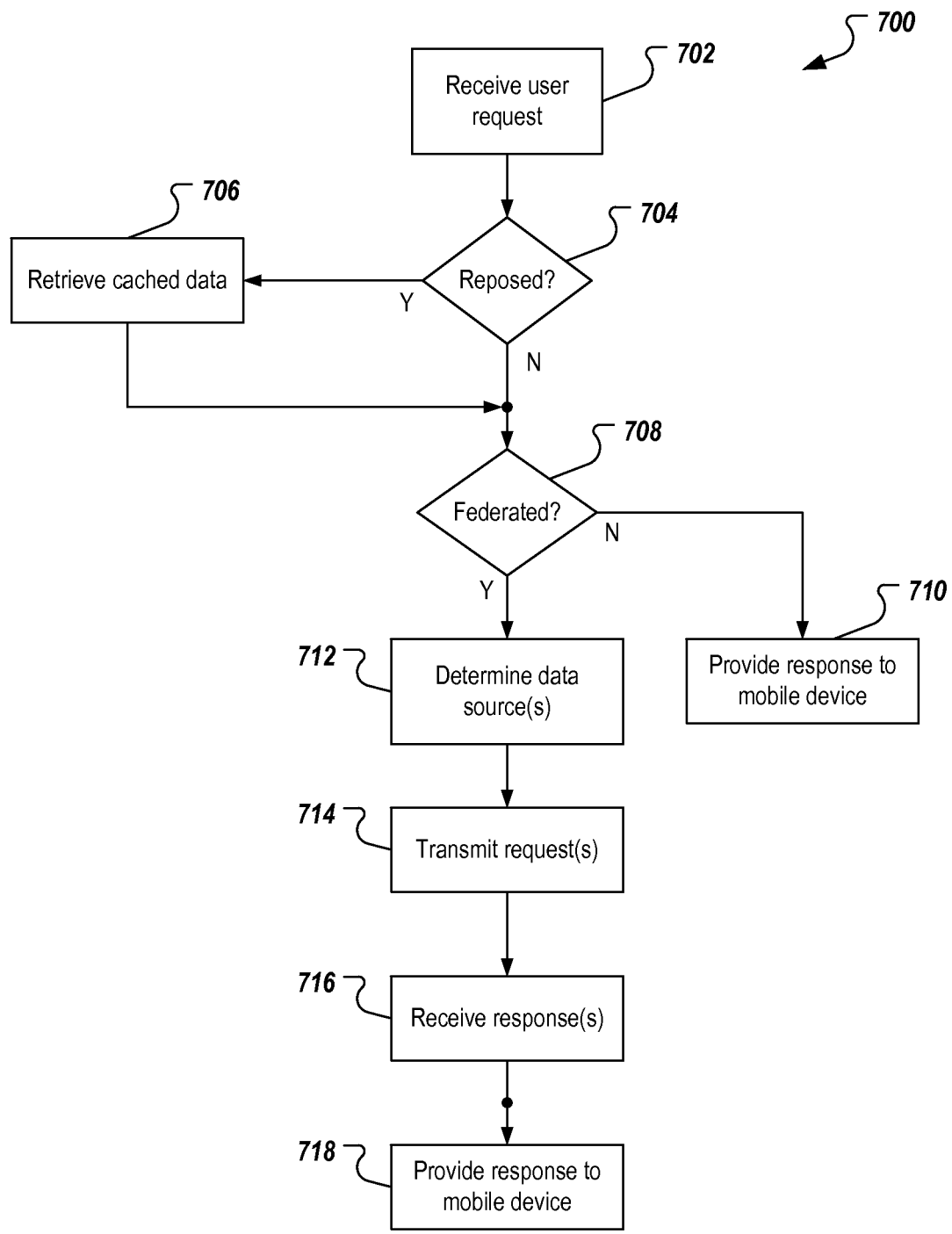
FIG. 7 is a flowchart illustrating an example process that can be executed in accordance with implementations of the present disclosure.

FIG. 7 depicts an example process 700 that can be executed in accordance with implementations of the present disclosure. In some examples, the example process 700 can be provided in one or more computer-executable programs that can be executed using one or more computing devices (e.g., DMS 160 and/or the DMS 180).

A user request is received (702). For example, the DMS 301 of FIG. 3 can receive a user request from the mobile device 102. It is determined whether at least a portion of the user request can be fulfilled in the reposed mode (704). For example, it can be determined that at least some patient data and/or patient information being requested can be provided from a local data store (cache). If it is determined that at least a portion of the user request can be fulfilled in the reposed mode, cached data is retrieved (706) (e.g., by the data cache module 314 of FIG. 3). If it is determined that at least a portion of the user request cannot be fulfilled in the reposed mode, it is determined whether the request, or at least a portion thereof, can be fulfilled in the federated mode (708). If it is determined that the request, or at least a portion thereof, cannot be fulfilled in the federated mode, a response is provided to the mobile device (710). In some examples, the response is based only on cached data that was retrieved (e.g., the reposed mode).

If it is determined that the request, or at least a portion thereof, can be fulfilled in the federated mode, one or more data source(s), from which patient data and/or patient information are to be retrieved are identified (712). One or more requests are transmitted (714). For example, the adapter module 316 of FIG. 3 can route requests to appropriate data sources for fulfilling the user request. One or more responses are received (716). For example, the adapter module receives responses from each of the data sources, from which patient data and/or patient information was requested. A response is provided to the mobile device (718). For example, responses from the data sources can be processed by the DMS 301, as discussed above, to provide a response to the user request to the mobile device 102. In some examples, the response can include patient data and/or patient information provided from the federated mode only, or provided from the reposed mode and the federated mode.

Figure 8:
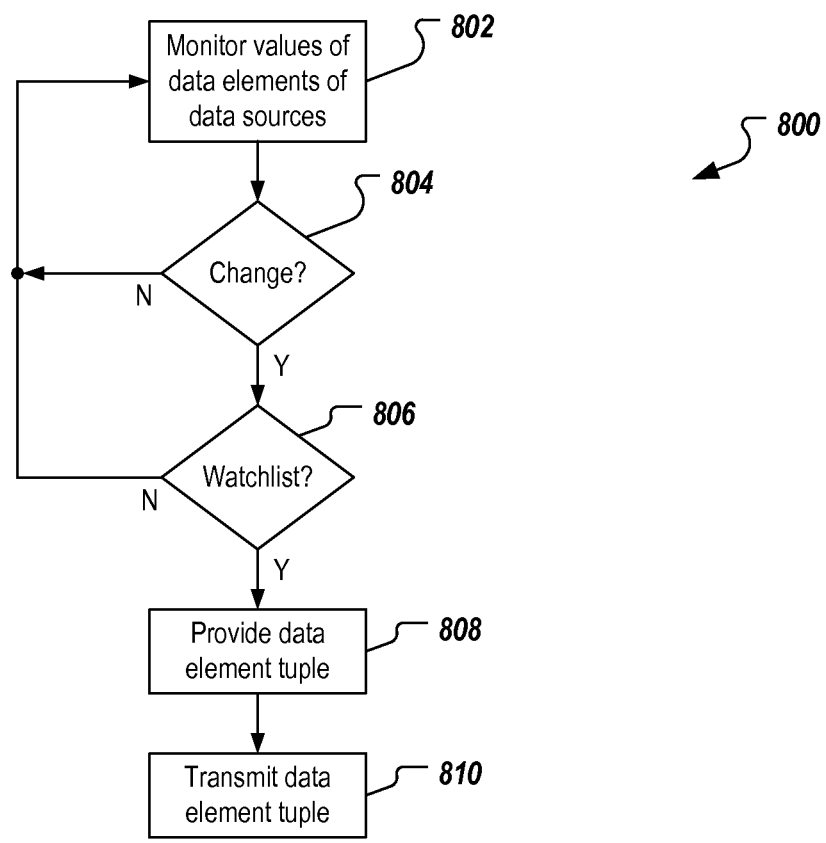
FIG. 8 is a flowchart illustrating an example process that can be executed in accordance with implementations of the present disclosure.

FIG. 8 depicts an example process 800 that can be executed in accordance with implementations of the present disclosure. In some examples, the example process 800 can be provided in one or more computer-executable programs that can be executed using one or more computing devices (e.g., DMS 160 and/or the DMS 180). In some implementations, the example process 800 can be executed in parallel with the example process 700 of FIG. 7. That is, for example, while the example process 700 is performed to provide patient data and/or information to a computing device (e.g., the mobile device 102), the example process 800 can be performed to provide patient data and/or information to a third-party system (e.g., the third-party analysis system 170).

Values of data elements of data sources are monitored (802). For example, and with reference to FIG. 5, a platform component 514, 516 can monitor data values of one or more data elements provided from data sources 506*a*, 506*b*, 508*a*, 508*b*, 510*a*, 510*b*, 512*a*, 512*b* (e.g., the data component can periodically poll a data source, the data source can periodically provide data values to the data component). It is determined whether a value of at least one data element has changed (804). If a value of at least one data element has not changed, the example process 800 loops back to continue monitoring of values of data elements.

If a value of at least one data element has changed, it is determined whether the data element is provided in a watchlist (806). For example, the platform component 514, 516 can compare the data element to one or more watchlists 518, 520 to determine whether the data element is present in at least one watchlist 518, 520. If the data element is not present in a watchlist, the example process 800 loops back. If the data element is present in a watchlist, a data element tuple corresponding to the data element is provided (808). For example, the platform component 514, 516 populates a data element tuple to include [Name, Date_Source, SourceID, StandardID, V, T]), as provided from a respective data source. The data element tuple is transmitted to a third-party system (810). For example, the platform component 514, 516 transmits the data element tuple to the third-party analysis system 170 over the network 106.

As described herein, implementations of the present disclosure enable near-real-time communication of patient physiological data to one or more third-party systems. In some examples, a third-party system is provided as a third-party analysis system that processes the patient physiological data to determine one or more analysis results. In some examples, an analysis result corresponds to a clinical score, a measure and/or a condition. For example, the third-party analysis system can process received patient physiological data to provide an analysis results that includes a diagnosis a respective patient with a condition. In some examples, the analysis result is provided to one or more healthcare providers. For example, the third-party system can provide the analysis result to the federated platform, which can provide the analysis result to one or more computing devices associated with respective healthcare providers (e.g., to a mobile device of a doctor). In this manner, the computational power of a third-party system can be leveraged to support functionality provided by the federated system, which can provide patient information and patient physiological data to healthcare providers in parallel, as described herein.

Implementations of the present disclosure can be provided using digital electronic circuitry, or in computer hardware, firmware, software, or in combinations thereof. In some examples, implementations can be provided one or more computer program products, e.g., a computer program tangibly embodied in a machine-readable storage device, for execution by, or to control the operation of, data processing apparatus, and/or a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Such a computer program can include modules and/or code segments for executing one or more of the features, aspects and/or implementations provided herein.

Operations in accordance with implementations of the present disclosure can be performed by one or more programmable processors executing a computer program product to perform functions by operating on input data and generating output. By way of example, a computer program product can include modules and/or code segments corresponding to each of the method steps, aspects and/or features provided herein. Method steps can also be performed by, and apparatus of the present disclosure can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer can include a processor for executing instructions and one or more memory devices for storing instructions and data. Generally, a computer can also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks such as internal hard disks and removable disks; magneto-optical disks; and CD-ROM and DVD-ROM disks. The processor and the memory can be supplemented by, or incorporated in special purpose logic circuitry.

The present disclosure can be implemented in a system including, but not limited to the example systems described herein, which include a back-end component, e.g., as a data server, or that includes a middleware component, e.g., an application server, or that includes a front-end component, e.g., a client device, such as the mobile device 102, having a graphical user interface or a Web browser through which a user can interact with an implementation of the invention, or any combination of such back-end, middleware, or front-end components. The components of the system can be interconnected by any form or medium of digital data communication, e.g., a communication network.

A number of implementations have been described. Nevertheless, it will be understood that various modifications may be made without departing from the spirit and scope of the disclosure. For example, steps of the present disclosure can be performed in a different order and still achieve desirable results. Accordingly, other implementations are within the scope of the following claims.

The invention claimed is:

1. A computer-implemented method for providing patient data to a third-party system in near-real-time, the method being executed using one or more processors and comprising:

determining, by the one or more processors, a change of a value of a data element within a patient data source of a facility system from a plurality of facility systems, wherein the plurality of facility systems form a healthcare continua and provide services for monitoring and treating a plurality of patients;

triggering, by the change of the value of the data element within the patient data source, an update of reposed patient data stored by a data cache module that is logically separated from the plurality of facility systems, the data cache module being configured to selectively operate in a pass-through mode and a reposed mode to improve performance of transmission of the patient data, the pass-through mode enabling real-time mode retrieval of the patient data from the facility system by using data identifiers and passing the patient data onward in response to a change and the reposed mode enabling transmission of a copy of the patient data temporarily stored by the data cache module;

determining, by the one or more processors, that the data element is included in a watchlist, the watchlist comprising one or more topics, each topic being associated with at least one data element;

providing, by the one or more processors, a data element tuple associated with the data element that is included in the watchlist;

performing, by the one or more processors, based on determining that the data element is included in the watchlist, a security check of a network connection and of the third-party system identified by the watchlist to determine that the third-party system is approved for receiving the patient data, the third-party system being accessible by a validated and authenticated healthcare provider; and transmitting, by the one or more processors, based on determining that the third-party system is approved for receiving the patient data, the data element tuple to a federated system to:

format the data element tuple by integrating a plurality of portions of the patient data from the plurality of facility systems in a single federated feed, filtering the patient data based on semantic mapping, and conditioning the data element tuple, to optimize transmission to the third-party system, translate the data element tuple from a vendor specific format to a standard format based on a vocabulary service that matches data types with different terminologies, and transmit the data element tuple in the standard format to the third-party system over a network for display in near-real-time on the third-party system.

2. The method of claim 1, wherein the data element tuple comprises a name, a data source name, a source identifier, and a standard identifier.

3. The method of claim 2, the name is provided as a human-readable name for the data element, the patient data source name indicates the patient data source and/or a type of the patient data source, the source identifier indicates a first identifier assigned to the patient data source, and the standard identifier comprises a second identifier for the data element using an applicable healthcare standard vocabulary.

4. The method of claim 1, wherein the watchlist is provided as a computer-readable file.

5. The method of claim 1, wherein determining that the data element is included in a watchlist comprises:

comparing information provided from the patient data source to information provided in the watchlist; and determining that the information provided from the patient data source matches the information provided in the watchlist.

6. The method of claim 1, wherein the watchlist is specific to the third-party system and comprises connection data for the third-party system.

7. The method of claim 6, wherein the connection data comprises an Internet Protocol (IP) address and a transmission control protocol (TCP) port number assigned to the third-party system.

8. The method of claim 1, wherein the watchlist is one of a plurality of watchlists, each watchlist corresponding to a respective third-party system.

9. The method of claim 1, wherein one or more topics comprise one of a clinical score, a measure and a condition, each of which is determined based on at least one value of at least one data element.

10. A non-transitory computer-readable storage device coupled to one or more processors and having instructions stored thereon which, when executed by the one or more processors, cause the one or more processors to perform operations for providing patient data to a third-party system in near-real-time, the operations comprising:

determining, by the one or more processors, a change of a value of a data element within a patient data source of a facility system from a plurality of facility systems, wherein the plurality of facility systems form a healthcare continua and provide services for monitoring and treating a plurality of patients;

triggering, by the change of the value of the data element within the patient data source, an update of reposed patient data stored by a data cache module that is logically separated from the plurality of facility systems, the data cache module being configured to selectively operate in a pass-through mode and a reposed mode to improve performance of transmission of the patient data, the pass-through mode enabling real-time mode retrieval of the patient data from the facility system by using data identifiers and passing the patient data onward in response to a change and the reposed mode enabling transmission of a copy of the patient data temporarily stored by the data cache module;

determining, by the one or more processors, that the data element is included in a watchlist, the watchlist comprising one or more topics, each topic being associated with at least one data element;

providing, by the one or more processors, a data element tuple associated with the data element that is included in the watchlist;

performing, by the one or more processors, based on determining that the data element is included in the watchlist, a security check of a network connection and of the third-party system identified by the watchlist to determine that the third-party system is approved for receiving the patient data, the third-party system being accessible by a validated and authenticated healthcare provider; and transmitting, by the one or more processors, based on determining that the third-party system is approved for receiving the patient data, the data element tuple to a federated system to:
- format the data element tuple by integrating a plurality of portions of the patient data from the plurality of facility systems in a single federated feed, filtering the patient data based on semantic mapping, and conditioning the data element tuple, to optimize transmission to the third-party system,
- translate the data element tuple from a vendor specific format to a standard format based on a vocabulary service that matches data types with different terminologies, and
- transmit the data element tuple in the standard format to the third-party system over a network for display in near-real-time on the third-party system.

11. A system, comprising:
one or more processors; and
a computer-readable storage medium in communication with the one or more processors and having instructions stored thereon which, when executed by the one or more processors, cause the one or more processors to perform operations for providing patient data to a third-party system in near-real-time, the operations comprising:

determining, by the one or more processors, a change of a value of a data element within a patient data source of a facility system from a plurality of facility systems, wherein the plurality of facility systems form a healthcare continua and provide services for monitoring and treating a plurality of patients;

triggering, by the change of the value of the data element within the patient data source, an update of reposed patient data stored by a data cache module that is logically separated from the plurality of facility systems, the data cache module being configured to selectively operate in a pass-through mode and a reposed mode to improve performance of transmission of the patient data, the pass-through mode enabling real-time mode retrieval of the patient data from the facility system by using data identifiers and passing the patient data onward in response to a change and the reposed mode enabling transmission of a copy of the patient data temporarily stored by the data cache module;

determining, by the one or more processors, that the data element is included in a watchlist, the watchlist comprising one or more topics, each topic being associated with at least one data element;

providing, by the one or more processors, a data element tuple associated with the data element that is included in the watchlist;

performing, by the one or more processors, based on determining that the data element is included in the watchlist, a security check of a network connection and of the third-party system identified by the watchlist to determine that the third-party system is approved for receiving the patient data, the third-party system being accessible by a validated and authenticated healthcare provider; and transmitting, by the one or more processors, based on determining that the third-party system is approved for receiving the patient data, the data element tuple to a federated system to:
- format the data element tuple by integrating a plurality of portions of the patient data from the plurality of facility systems in a single federated feed, filtering the patient data based on semantic mapping, and conditioning the data element tuple, to optimize transmission to the third-party system,
- translate the data element tuple from a vendor specific format to a standard format based on a vocabulary service that matches data types with different terminologies, and
- transmit the data element tuple in the standard format to the third-party system over a network for display in near-real-time on the third-party system.

\* \* \* \* \*